United States Patent [19]
Said et al.

[11] 4,113,711
[45] Sep. 12, 1978

[54] VASOACTIVE LUNG POLYPEPTIDES

[76] Inventors: Sami I. Said, 5323 Harry Hines Blvd., Dallas, Tex. 75235; Viktor Mutt, Karolinska Institutet, Stockholm, Sweden

[21] Appl. No.: 649,968

[22] Filed: Jan. 19, 1976

[51] Int. Cl.$^2$ .................. B66F 1/04; A61K 37/00; C07C 103/52
[52] U.S. Cl. .................. 260/112 R; 424/177; 260/112.5 R
[58] Field of Search .................. 260/112.5 R, 112 R; 424/177

[56] References Cited
U.S. PATENT DOCUMENTS

| | | | |
|---|---|---|---|
| 3,862,927 | 1/1975 | Said et al. | 260/112.5 R |
| 3,879,371 | 4/1975 | Said et al. | 260/112.5 R |
| 3,880,826 | 4/1975 | Said et al. | 260/112.5 R |
| 3,898,329 | 4/1975 | Said et al. | 424/177 |

OTHER PUBLICATIONS
Said et al.: Nature: 224, 699–700 (1969).
Said et al.: Science, 169, 1217–1218 (1970).

Primary Examiner—Delbert R. Phillips
Attorney, Agent, or Firm—Lowe, King, Price & Markva

[57] ABSTRACT

Vasoactive polypeptide fractions having biological activity isolated in purified form from animal lungs induce peripheral vasodilation and systemic hypotension. One of the peptides exhibits the property of relaxing isolated non-vascular smooth muscle organs while the other peptide contracted these tissues. The peptide fractions are obtained from the lungs of animals by procedures involving boiling and mincing the lung, extracting the peptides into acetic acid, adsorbing by alginic acid, eluting with HCl and salting out, extracting into alcohol, again adsorbed with alginic acid, fractionating by gel chromatography, e.g. on Sephadex G-25, and by ion exchange chromatography, e.g. on carboxymethyl cellulose, followed by further ion exchange chromatography and, optionally, countercurrent distribution.

1 Claim, 5 Drawing Figures

VASOACTIVE LUNG POLYPEPTIDES

The invention described herein was made in the course of work under a grant or award from the Department of Health, Education and Welfare.

BACKGROUND OF THE INVENTION

1. Field of the Invention

This invention relates generally to new polypeptide fractions, their methods of isolation, biological actions of the peptides, and therapeutic usefulness. More particularly, the present invention relates to new polypeptide fractions isolated from the lungs of animals, and more particularly from the lungs of hogs by novel purification procedures, and to the wide-range of biological activities of the polypeptides.

2. Description of the Prior Art

It is well-known that polypeptide hormones regulate many physiologic functions and mediate certain pathological responses. While numerous compounds have been known to possess a vasodilator effect, many possess this effect only to a relatively slight degree or for a very short time. Medical science has, therefore, sought materials exhibiting a more potent or sustained vasodilator effect which would be more useful therapeutic agents.

In Prior U.S. Pat. Nos. 3,879,371, 3,880,826, 3,862,927 and 3,898,329 of the present inventors, there is disclosed a vasoactive peptide and its method of isolation from the upper intestinal wall of porcine. The porcine vasoactive intestinal peptide was identified as an octacosapeptide of specific sequence which exhibited biological activity in the areas of systemic vasodilation, hypotension, increased cardiac output, respiratory stimulation and hyperglycemia. A report on this peptide and its method of isolation may be found in the literature in Science, pps. 169, 1217–1218 (1970). Another publication of interest to the porcine vasoactive peptide may be found in Eur. J. Biochem., pp. 42, (1974).

The present inventors have previously published articles covering their earlier work regarding peptides present in lung tissue which exhibited vasodilator effects. Thus, in *The Scandinavian Journal of Clinical & Laboratory Investigation,* Vol. 24, Suppl. 107, pp. 51—56 (1969), it was reported that a peptide fraction had been obtained from lung tissue of hogs which had prolonged peripheral vasodilator activity. Also, in Nature, Vol. 224, No. 5220, pp. 699–700, (1969), there was reported the occurrence in lung tissue of normal hogs, the presence of a vasoactive peptide having a prolonged systemic vasodilator effect. This peptide is indicated as being extractable in a relatively purified form. In the publication *Chemistry and Biology of Peptides,* pp. 409–414, (1972), the present inventors reported that efforts to isolate a vasoactive polypeptide from hog lungs had led to the extraction and partial purification of two biologically active peptide fractions which are dilators of peripheral systemic and pulmonary vessels, and have activity on non-vascular smooth muscle.

The present invention is concerned with highly purified vasoactive polypeptide fractions which have been isolated from the lungs of animals such as hogs and which exhibit biological activity in inducing peripheral vasodilation and systemic hypotension.

SUMMARY OF THE INVENTION

It is accordingly a main object of the present invention to provide new polypeptides which exhibit important biological actions.

It is a further object of the present invention to provide new polypeptides which induce peripheral vasodilation and systemic hypotension.

A still further object of the invention is the provision of isolation and separation techniques for isolating polypeptides from lungs of mammals such as hogs through the use of extractive chromatography and other separation procedures.

A further object of the invention is the provision of therapeutic compositions of matter containing the new polypeptides.

A further object of the present invention is a provision of a method of treating humans and animals by administration of the new polypeptides.

These and other objects of the present invention will become apparent as the description thereof proceeds.

In satisfaction of the foregoing objects and advantages, there is provided by this invention vasoactive polypeptide fractions which have been isolated from the lungs of mammals such as hogs, which polypeptide fractions induce peripheral vasodilation and systemic hypotension. One of the peptides exhibits the property of relaxing isolated non-vascular smooth-muscle organs while the other peptide contracted these tissues. These peptides are isolated from the lungs of mammals such as hogs and are purified by a process including the steps of obtaining the lungs in the minced and frozen state, freed of pancreatic tissue, extracting with acetic acid, adsorbing on alginic acid, eluting with acid such as HCl, salting out, extracting into alcohol, fractionating by gel chromatography, e.g. on Sephadex G-25, and by ion exchange chromatography, e.g. carboxymethyl cellulose, one or more times, optionally subjecting to countercurrent distribution, and collecting the purified peptides. There are also provided therapeutic compositions of matter containing the peptides and use of the therapeutic compositions to produce useful biological actions by administration thereof.

BRIEF DESCRIPTION OF THE DRAWING

Reference is now made to the drawings accompanying this application wherein.

DESCRIPTION OF PREFERRED EMBODIMENTS

The present invention is concerned with the isolation, purification, characterization and biological uses of new vasoactive polypeptides which have been isolated from animal lungs and which have been found to be potent in a number of biological areas.

Although abnormal lung tissue, especially lung tumors, may elaborate a variety of polypeptide hormones, none has been isolated from normal lung. Two biologically active peptide fractions have now been partially purified from fresh, blood-free, lungs of hogs. The procedures for their preparation included boiling and mincing of lung, extraction of peptides in acetic acid, their adsorption on alginic acid, elution with HCl, salting out, extraction into a lower alkyl alcohol, fractionation one or more times by gel chromatography, e.g. on Sephadex G-25, and fractionation one or more times by ion exchange chromatography, as on carboxymethyl cellulose, and optionally countercurrent distribution. Both peptides induced peripheral vasodilation and systemic hypotension in anesthetized dogs. One peptide also relaxed isolated non-vascular smooth muscle organs, including guinea pig trachea and gallbladder, rat stomach and chick rectum, while the other contracted these tissues. The smooth muscle relaxing peptide shares these biological properties with the recently isolated vasoactive intestinal polypeptide described above, but possible structural similarities have not been ascertained. The actions of the smooth muscle contracting peptide resemble those of prostaglandins, and thus it may be mistaken for these compounds on bioassay. These lung peptides appear to participate in the regulation of normal airway and pulmonary vascular reactions, and in embolism and anaphylaxis.

As indicated above, the vasoactive lung polypeptides of this invention are isolated from the lungs of animals and in the particular embodiment disclosed, have been isolated from the lungs of hogs. The products were isolated by procedures involving collecting the lungs immediately after the animals are slaughtered and examining the lungs to insure that they are free of infection, hemorrhage or edema. If the collection is delayed for any reason, ice should be placed over the lungs or they should be kept in a cool room. The lungs are then rinsed with running water and cut into thin slices to facilitate boiling and mincing and any fat present is removed. For boiling, a plated metal vessel is filled with water and a steam pipe placed deep in the water. When the water boils, a basket containing the lungs is fixed in the metal vessel and the lungs are left under boiling conditions for a short period, e.g. about 5 to 15 minutes, then taken out cooled quickly. The boiled lungs are then minced, placed in bags and weighed. Each bag is sealed, flattened and identified. The bags are then immediately placed in a freezing room at $-18°$ C. and by this way the fresh lungs are collected.

The crude lung material is then weighed and extracted with acetic acid by placing 1 kg of the crude material in 40 liters of water and diluting with acetic acid to make-up a 2–5% solution. The frozen crude material is broken into pieces after weighing and extracted by leaving the lungs in the acid solution with constant stirring at a temperature of about 0–5° C. for an extraction period of about 20–24 hours.

The resulting extraction mixture is then filtered by adding Hyflo Super Cel to the extraction mixture and filtering through a large suction filter and refiltered until almost clear.

The extracted mixture is then subjected to alginic acid adsorption at a ratio of about 50 grams alginic acid for each kilogram of the crude extract. In this procedure the filtrate collected from the acetic acid extraction step is collected, and will be found to have a pH of about 3.4 which is then brought down to a pH of about 2.7 with 2N HCl. The filtrate is stirred with the alginic acid until the picric acid reaction shows that it is relatively free of peptides and there is no sediment. The alginic acid containing the lung material is then allowed to settle and the supernatant liquid discarded, and the sediment transferred onto a suction filter. The sediment is washed several times with dilute HCl, then with alcohol to remove fats, and the alcohol washed out with 0.005 N HCl.

The peptide material is eluted from the alginic acid with 0.2 N HCl by stirring under the same suction filter and until the picric acid test is negative. At this point of the process, sodium chloride is added to the eluate to saturate each liter of the eluate. The mixture is then stirred for a short period, left overnight, and the precipitate collected on the suction filter and dried and the collected salt precipitate kept in a vessel and placed in the freezer. When the material has been eluted with the alginic acid, the latter is washed with 0.2 N HCl several times to remove all traces of the lung material, then with 0.05 N HCl several times. This is done on a suction filter with the last washing being sucked as dry as possible. The alginic acid can be used repeatedly up to at least 10 times for this purpose. It will be observed that for every kilogram of extracted crude material there will be recovered about 2–3 grams of collected salt precipitate.

The collected salt precipitate is then extracted with alcohol, preferably methanol by dissolving the salt precipitate in water at a ratio of about 10 milliliters per gram, with the practical amount by weight of the collected salt to be dissolved being about 50–60 grams. The resulting solution is neutralized to a pH of 7 with a base such as an alkali metal hydroxide, heated by vigorous stirring and additional precipitate will be observed near the neutral pH point. The resulting mixture is then extracted with a lower alkyl alcohol such as methanol and stirred for a short period. This extract is then filtered through large glass filters, with the filtered volume being mixed with ice and water and stirred in a large vessel with the pH, which is now 7, then being brought down to about 2.7 with mineral acid, preferably HCl, such as 2 N HCl. It will be observed that for every 50 grams of collected salt material extracted with alcohol there will be recovered 2–3 grams of alcohol extract.

The alcoholic extract material is then subjected to chromatography over Sephadex G-25 or other cross-linked dextran or similar gel at least once and preferably two times. According to this method of purification, the peptide from the alcoholic extraction is subjected to a chromatographic separation in the presence of a gel such as a cross-linked dextran, e.g., Sephadex G-25, in a column which has been previously washed with acetic acid. This gel chromatography separation is utilized to separate the various polypeptide molecules in accordance with their size. The column may be Sephadex, which is a well-known cross-linked dextran frequently used for this purpose, or cellulose or a like gel filtration medium. The crude extract from the previous step is dissolved in an organic acid such as acetic acid. The concentration of the acid is not critical but may vary from approximately 0.1M to 0.3M. The preferred organic acid is acetic acid. From this chromatographic step, fractions are collected beginning with the introduction of the polypeptide solution into the column. Fractions are then combined and saturated with sodium chloride and the material salted out and re-precipitated. The chromatography over Sephadex G-25 is a well known procedure and is described for example in our prior patents concerned with the vasoactive polypeptide described above.

The fractions from the gel chromatography are collected in two parts and the most active fractions, as tested on femoral blood flow of anesthetized dogs and on isolated smooth-muscle organs, are then subjected to chromatography on carboxymethyl cellulose or similar ion exchange chromatography at least once. In conducting this chromatographic step, the active fractions are dissolved in a buffer solution such as phosphate buffer and the pH adjusted to 6-7 by the addition of a base such as alkali metal hydroxide. The mixture is centrifuged to eliminate any insoluble material, fractions collected and then treated with alginic acid for adsorption of peptides and later eluted with mineral acid. The resulting fractions are then freeze-dried and the active fractions identified. In the most preferred procedures the active fractions are combined and subjected to further ion exchange chromatography to obtain highly purified fractions.

The ion-exchange chromatography separation preferably utilizes carboxymehtyl cellulose (CMC), though other ion-exchange media may be utilized. The buffer may be an alkali metal (Na, $NH_4$) carbonate or bicarbonate, phosphate or acid phosphate. The concentration of the buffer is not critical but preferably may vary between approximately 0.01 and 0.015M. The pH of the buffer solution should be between 6 and 7, preferably between 6.2 and 6.6. The solution is allowed to pass through the column with elution carried out by linear gradients.

The most active fraction was identified and characterized as being active both on blood flow (vasodilator) and on smooth muscle organs (Spasmogenic). The next most active fraction was found to relax gastric and tracheal smooth muscles.

During the earlier steps of extraction and purification, test solutions were assayed only by their vasoactivity. This was measured by monitoring femoral blood flow and aortic blood pressure in anesthetized dogs, on infusing the extracts into a branch of the femoral artery. During later purification, peptide fractions were also assayed by their effects on isolated, superfused smooth-muscle organs.

The active peptide fractions induced peripheral vasodilation, evidenced by an increase in femoral blood flow with a fall in aortic blood pressure. When tested on smooth-muscle organs, the vasoactive peptide fractions were found to contain at least two active principles, having opposite actions. Thus, one fraction contracted, and the other relaxed these tissues: stomach strip and colon of rat; trachea, ileum and gallbladder of guinea pig; and chick rectum. The smooth-muscle relaxing potency was increased several fold after countercurrent distribution. These tissue responses were unaltered by pharmacologic blockade of histamine, 5-hydroxytryptamine, adrenergic or cholinergic receptors.

The smooth-muscle actions of the spasmogenic lung peptide mimic those of the prostaglandins and prostaglandin-related compounds. Prostaglandin $E_1$ and $E_2$, for example, contract rat stomach strip and colon, guinea pig gallbladder and chick rectum. Prostaglandin $F_2\alpha$ contracts guinea pig trachea in addition to contracting the other tissues to a greater (e.g., colon), or smaller (e.g., gallbladder), extent.

BIOLOGICAL EFFECTS

The active peptide fractions isolated according to the above procedure were found to be useful in several important areas. These properties were determined in two different systems:

(1) Intact anesthetized dogs:

In this characterization the fractions were infused into one femoral artery, and the blood flow in that artery as well as the aortic blood pressure were continually measured. During the infusion of the peptide, the blood pressure fell and the blood flow increased indicating peripheral vasodilation. The effects were relatively prolonged lasting approximately 15-30 minutes with the infusion of 1-10 microgram per minute for 1 minute. For assay of vasoactivity the hind limb of anesthetized dogs is used by injecting the extract preparation into a cannulated branch of the femoral artery and measuring the increase in flow by an electromagnetic probe placed around the main artery. Simultaneously, the means systemic arterial blood pressure is recorded by a catheter in the aorta and a strain gauge transducer.

(2) Isolated smooth-muscle organs:

In this characterization strips of smooth-muscle organs, rat stomach, rat colon, guinea pig trachea, ileum, guinea pig gallbladder, and chick rectum were placed in series and superfused with warm physiological solution (Krebs), bubbled with 95% oxygen, and 5% $CO_2$. The organ strips were attached to special transducers which measured their contraction or relaxation. The addition of the active fractions isolated as described herein to the physiological solution caused relaxation of stomach, trachea, and other tissues. One of the active fractions contracted the smooth-muscle organs such as rat stomach strip, rat colon, guinea pig ileum, trachea, gallbladder, pulmonary artery, and guinea pig "lung". On the other hand, the second active fraction relaxed these tissues. A description of this test may be found in "The American Journal of Medicine," September, 1974, pages 452-465, by Sami I. Said. Generally in the technique of organ superfusion, perfusate from isolated lung is allowed to drip on the series of isolated smooth-muscle organs, whose responses are recorded continuously by transducers. The lung is perfused with physiologic solution or blood, driven at a steady flow rate, and is ventilated by means of a pump connected to the airway. The preparation is suitable for investigating the effects of several variables on the activity of the sensitive smooth-muscle organs, and samples of perfusate also may be collected for subsequent analysis. Variables under examination may include changes in tidal volume, frequency, inspired oxygen concentration, perfusion pressure or outflow (venous) pressure and induction of pulmonary embolism, edema or anaphylaxis.

Because of the characteristics of the active polypeptides these materials are useful in a number of important areas. Thus, as they effect the cardiovascular system, they affect peripheral systemic vasodilation, lower blood pressure and relax the bronchial smooth-muscle. Also, the peptides exhibit excellent smooth-muscle activities.

The potent vasodilator action of the peptides suggest usefulness in promoting peripheral blood flow in extremities, and in relieving pulmonary hypertension in disease states associated with constriction of pulmonary vessels and in the relief of coronary angina pectoris. Because of the hypotensive action, the polypeptides suggest usefulness as an additional tool in the management of systemic hypertension. The smooth-muscle relaxant properties of the polypeptides render them useful in the management of excessive contractions of certain organs such as gallbladder, or bronchia (asthma).

DOSAGE AND ADMINISTRATION

It is recommended that the dosage to humans or animals be by intravenous injection of 0.02–10 µg per kg of body weight for most biological conditions. The carrier may be any physiologically safe and unreactive solvent, many of which are well known in the art. Among those considered useful are the normal saline solutions, THAM solution, and others. The concentration of peptide in the carrier may vary widely, e.g. from 0.001 to 0.10 weight percent.

The two active polypeptide fractions were distinguished in their activity in that while both peptides induced peripheral vasodilation and systemic hypotension in anesthetized dogs, only one of the peptides relaxed isolated non-vascular smooth-muscle organs including guinea pig trachea and gallbladder, rat colon and chick rectum whereas the other contracted these tissues. The actions of the smooth-muscle contracting peptide resemble those of prostaglandins and thus may be mistaken for these compounds on bioassay.

In the isolation of the polypeptide fractions, a several-fold increase in activity can be obtained by countercurrent distribution in normal butanol/0.1 M $NH_4HCO_3$. Alternatively, an additional chromatography step on carboxymethyl cellulose or other ion exchange material may precede the countercurrent distribution step.

The following examples are presented to illustrate the invention but it is not to be considered as limited thereto. In these examples and throughout the specification parts are by weight unless otherwise indicated.

EXAMPLE

In the following specific example, the alginic acid, Sephadex G-25 (fine) and carboxymethyl cellulose were obtained from commercial sources.

A. Collection of Lungs.

The hogs used were between 6–12 months of age. The hog lungs are collected immediately after the animals are killed and examined by a physician or a veterinarian to insure that they are free of infection, hemorrhage or edema. If the procedure of collection is delayed for any reason, ice should be placed all over the lungs, or lungs should be kept in the cool room. The lungs are rinsed with running water, then cut into thin slices to facilitate both boiling and mincing. Any fat present is removed. For boiling, a plated metal vessel is filled with water to a known point, and the steam pipe is placed deep in the water. When the water boils to 100° C., the basket containing the lungs is fixed in the metal vessel by special fittings. The lungs are left for 8–10 minutes, at the same temperature, then taken out and cooled quickly. The boiled lungs are minced, placed in nylon bags and weighed. Each bag is sealed with tape and flattened. Identifying information is written on each bag as to contents; weight; date; number and age of animals. These bags are immediately placed in a freezing room (−18° C.) and Step 2 is repeated for the duration of the slaughtering of hogs on that day (usually around 25 hogs per day). In this way, only fresh lungs are collected. The frozen lungs are not to be stored longer than 1 month.

B: Extraction of the Crude Material with Acetic Acid and Alginic Acid Adsorption.

1. Weighing and Extraction 10,000 Grams of the crude material needs 40 liters water for diluting 1200 ml acetic acid to make up a 3% solution. The frozen crude material is broken into pieces, weighed and extracted by leaving the lungs in the acid solution, with constant stirring, overnight in the cool room (+4° C.). The period of extraction was around 20–22 hours.

2. Filtration of the Extracted Mixture

Hyflo Super-Cel is added to the extraction mixture, which is then filtered through a large suction filter (2 layers of Whatman Paper No. 541). The filtrate is refiltered until it is almost clear. Two thousand grams of Hyflo Super-Cel were added which amounted to 2,000 grams Hyflo Super-Cel for every liter of the extracted mixture.

3. Adsorption to Alginic Acid

Fifty grams of alginic acid is needed for every kg of the crude extract and in this example, 500 grams of alginic acid were used for the amount of material treated. The filtrate was collected in a large plastic container. The pH is usually 3.4 and is brought to 2.7 with 2N HCl. The filtrate is stirred with the alginic acid until it is shown from the picric acid reaction to be relatively free of peptides (no sediment). The alginic acid containing the lung material was allowed to settle for one hour or slightly longer. The supernatant liquid was discarded and the sediment is transferred onto a suction filter (2 layers of Whatman Paper No. 541).

4. Washing of the Sediment

The sediment was washed several times with 0.005N HCl, then with 95% ethanol to remove fats; the ethanol was washed off several times with 0.005N HCl.

5. Eluting Peptides from Alginic Acid

The peptide material was eluted from the alginic acid with 0.2N HCl while stirring, using the same suction filter (2×541), and until the picric acid test is negative.

6. Collection of the Salt Precipitate

Sodium chloride was added to the eluate to the point of saturation, 320 grams of NaCl being needed to saturate each liter of the eluate. The mixture was stirred for 15–20 minutes, and then left until the next morning. The precipitate was collected on a suction filter and dried. The collected salt precipitate was kept in a beaker, weighed, dated, and left in the freezer.

7. Washing of the Alginic Acid

When the material has been eluted from the alginic acid, the latter is washed with 0.2N HCl several times to remove all traces of the lung material, then with 0.005N HCl several times. That is done on a suction filter, the last washing being sucked as dry as possible. The alginic acid could be used repeatedly for at least 10 times. When not in use it is stored in the frozen state. It is usually packed in nylon bags, properly labeled. It is observed that every kg of extracted crude material yields 2–3 g of the collected salt precipitate.

C. Methanol Extraction of the Salt Precipitate.

1. Formation of the Solution

The salt precipitate from "B" was dissolved in water in a ratio about 10 ml/g. Due to the limited size of the plastic vessels (100 liters) and laboratory space, the practical weight of the salt precipitate to be dissolved at a given time is 50-60 grams.

2. Neutralization of the Solution

The solution was neutralized to a pH of 7 by the addition of 0.1M sodium hydroxide, aided by vigorous stirring; and additional precipitate came out near the neutral pH.

3. Extraction with Methanol

The resulting mixture was then extracted in 20X volumes of methanol, and stirred for 15 minutes.

4. Filtration of the Extracted Mixture

The extracted mixture was then filtered through large glass filters using Whatman 00 filter paper. The filtered volume was mixed with 13.5 volumes of ice and $H_2O$, and stirred in a large plastic vessel (100 liters). The pH (7) was then brought down to 2.7 with 2N HCl.

D. Re-Extraction with Acetic Acid.

The acetic acid extraction of "B" was repeated as above except that, (a) butanol is also used in washing the sediment in between the several washings with ethanol, while stirring to remove fats; and (b) the eluate is refiltered through 00 paper before adding NaCl.

From these treatments there was recovered 2.3 grams of material suitable for chromatography.
Yield:

It was observed that 20 kg of fresh lungs gives 10 kg crude material, which gives around 25 grams salt precipitate, which in turn gives 0.75-1.50 grams of material suitable for chromatography.

E. Chromatography on Sephadex G-25, Fine.

Figure 1:
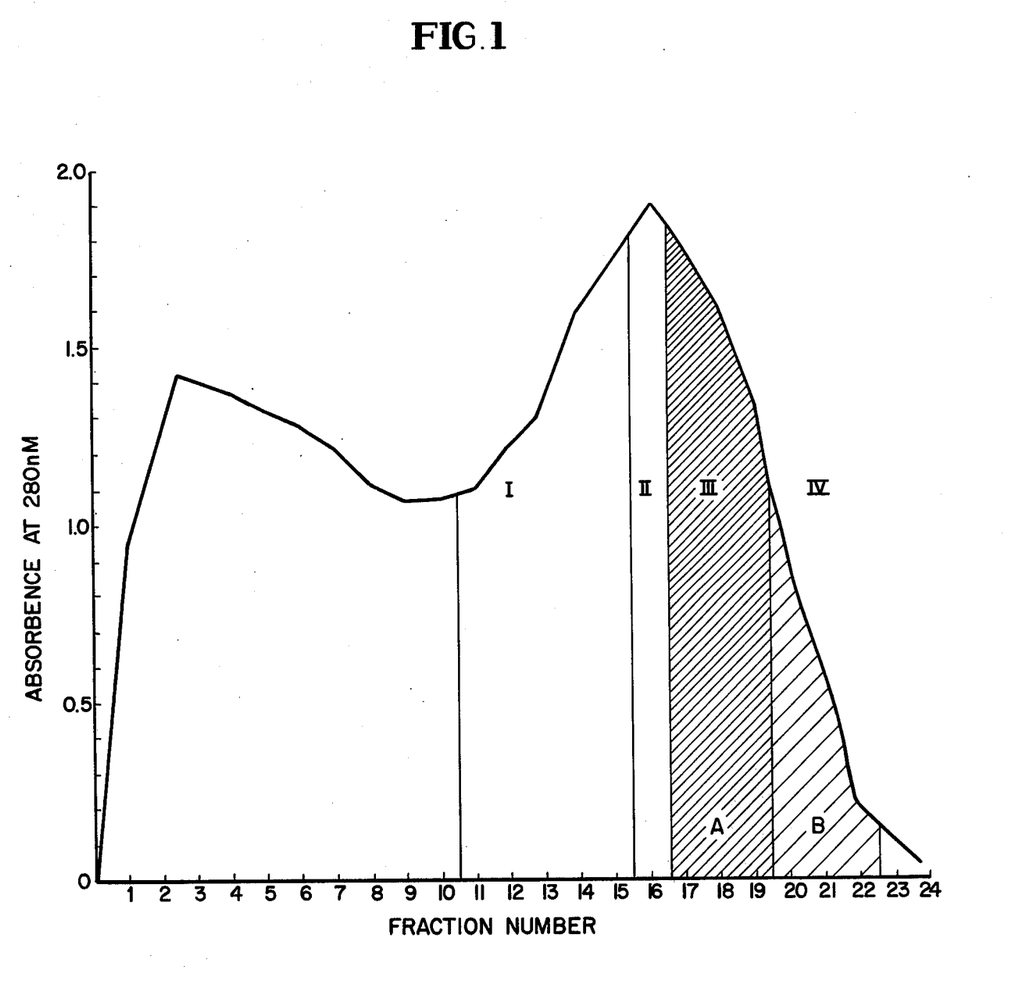
FIG. 1 represents a graph of the fractions obtained from gel chromatography on Sephadex G-25.

The columns used for this step were 95 × 10 cm in size and were loaded with Sephadex G-25, fine. 23.1 Grams of material from "D" was dissolved in 231 ml 0.2 M acetic acid. The "solution" was centrifuged to get rid of sediment (15 minutes, 12,000 rpm), and the clear solution (115 ml) placed on column. The conditions of the chromatography were as follows:

Void Volume: 2700 ml, fraction volume: 100 ml. The fractions were collected in two parts (columns A and B), as shown in chromatograms.
Weights of Fractions:

|  | Weights of Fraction: | | |
| --- | --- | --- | --- |
|  | Fractions | Column A | Column B |
| — | 1-10 | discarded | |
| I | (11-13) | 509 mg | 505 mg |
| II | (14-16) | 545 mg | 532 mg |
| III | (17-19) | 466.8 mg | 442 mg |
| IV | (20-22) | 134.7 mg | 96.6 mg |

FIG. 1, accompanying the application, is a plot of the chromatography on Sephadex G-25 wherein absorbence at 280nM is plotted against the fraction number. The most active fractions were fractions 17-19 and 20-22 as indicated by tests on femoral blood flow of anaesthetized dog and on isolated smooth muscle organs. Active fractions 17-19 and 20-22 are shown as shaded area A and hatched area B in FIG. 1, i.e. areas III and IV.

F. First Chromatography on Carboxymethyl Cellulose (CMC):

I. Fraction Nos. 17-22 from the Sephadex chromatography (1.14 g) were dissolved in 55 ml phosphate buffer and the pH was adjusted to 6.4 with 14 ml 0.03 M NaOH. The mixture was centrifuged to eliminate any insoluble material. Gradient buffer: Same + 0.3 M NaCl gradient. Fractions: 30 ml each, 1 fraction every 3 minutes Void Volume: 200 ml Fractions collected as shown in chromatogram of FIG. 2, then treated with alginic acid (for adsorption of peptides, which were later eluted with 0.2 M HCl). $Cl^-$ then exchanged for acetate$^-$ on a column of DEAE-Sephadex, and resultant corresponding fractions were freeze-dried (lyophilized). Volumes and Weights were:

| Areas of Fractions | Original Volume | Alginic Acid Eluate | Wt. after Ion-Exchange and Lyophilization |
| --- | --- | --- | --- |
| I | 155 ml | 205 ml | |
| II | 135 ml | 180 ml | |
| III | 150 ml | 195 ml | |
| IV | 135 ml | 185 ml | |
| V | 158 ml | 200 ml | |
| VI | 125 ml | 175 ml | 254.4 mg |
| VII | 115 ml | 155 ml | 79.5 mg |
| VIII | 185 ml | 180 ml | 19.5 mg |
| IX | 160 ml | 200 ml | 10.0 mg |

Figure 2:
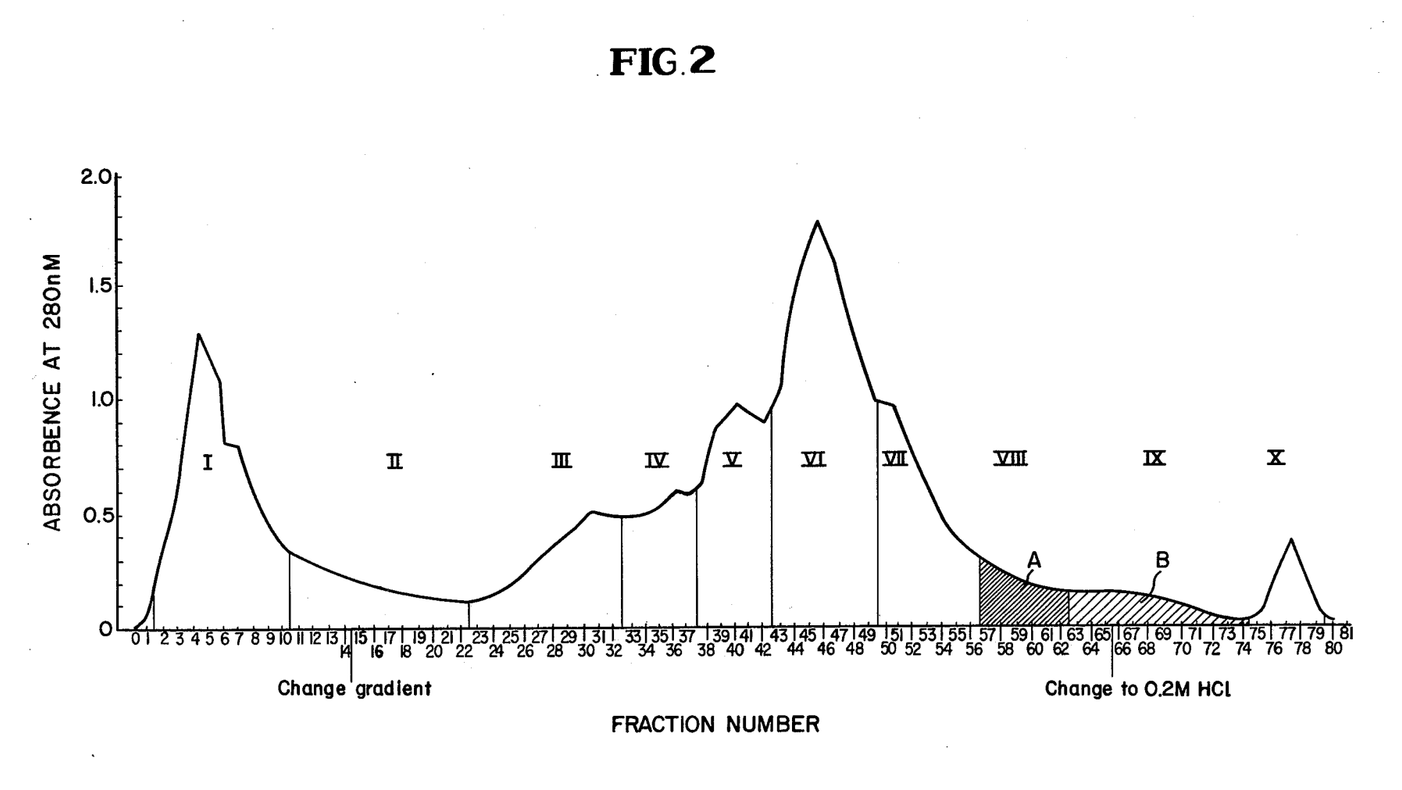
FIG. 2 represents a graph of the initial fractions obtained from first ion exchange chromatography on CM-celluose (CMC)

In FIG. 2, it will be observed that a plot of absorbence at 280nM against fraction number is known. The fractions are identified as areas, I, II, III, IV, V, VI, VII, VIII and IX.

The activity of the fractions as determined by tests on femoral blood flow of anesthetized dog and on isolated smooth muscle organs showed that fraction area IX (fractions 63-74) was the most active fraction, both on blood flow as a vasodilator and on isolated smooth muscle organs (Spasmogenic). Fraction area IX (fractions 63-74) is indicated as hatched area "B" in the graph of FIG. 2.

The next most active fraction was fraction area VIII (fractions 57-62) (vasodilator) as it relaxed gastric and tracheal smooth muscle. The fraction area VIII is indicated as shaded area "A" in the graph of FIG. 2.

Figure 3:
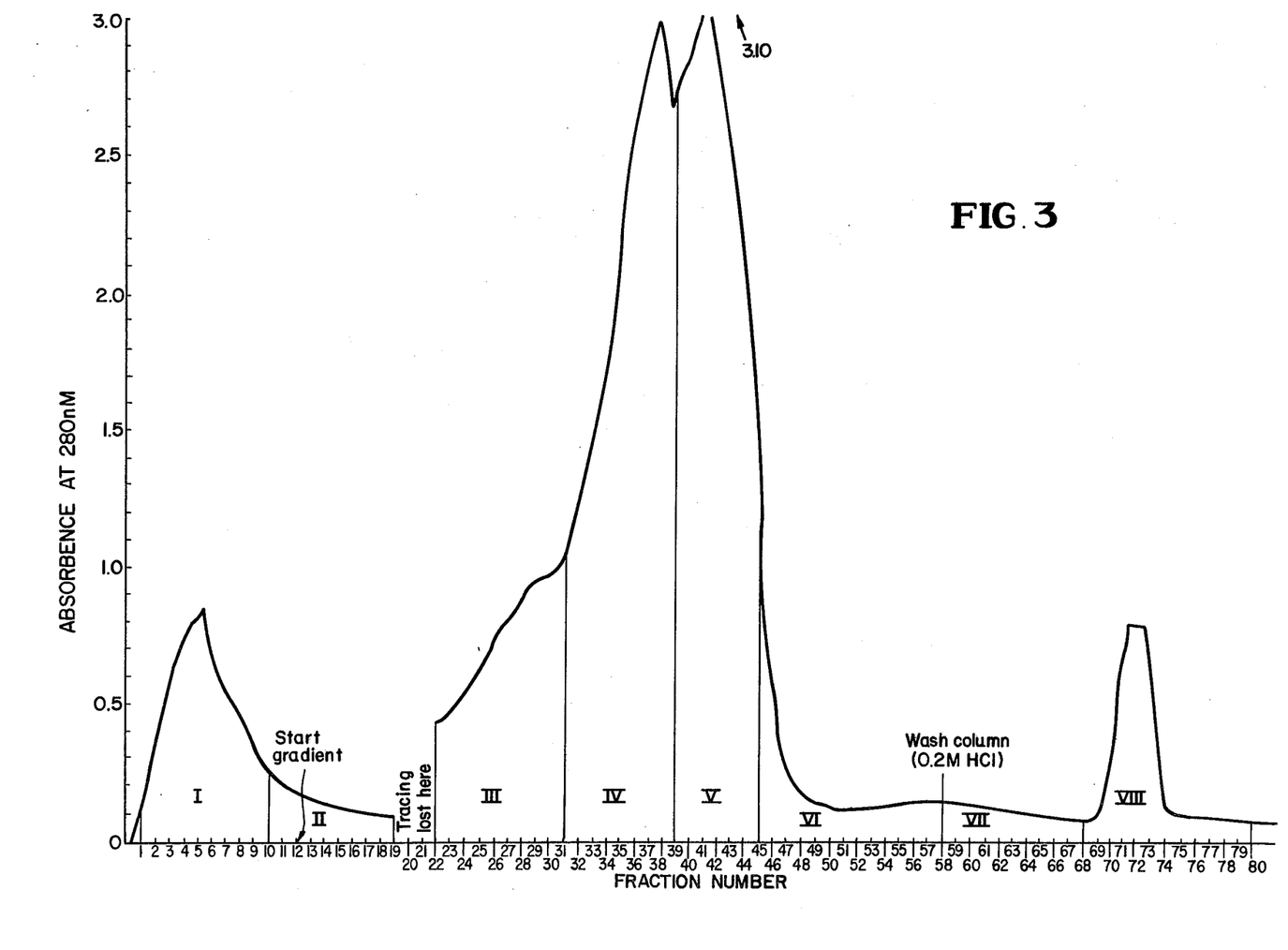
FIG. 3 represents a graph of the fractions obtained from ion exchange chromatography on CMC of fractions 11-16.

II. Fraction Nos. 11-16 from the same Sephadex column referred to above (I) (2.0g) were dissolved in 100 ml phosphate buffer and the pH was adjusted to 6.4 with 32 ml of 0.03 M NaOH. Developing buffer: same as above. Fractions: 30 ml each, 1 fraction every 3 minutes Void Volume: 190 ml Fractions were collected as shown in FIG. 3, then treated with alginic acid, ion-exchange chromatography (to replace $Cl^-$ with acetate$^-$), and the resultant corresponding fractions were freeze-dried. Volumes and weights were:

|  | Fractions | Wt. after Ion-Exchange and Lyophilization |
| --- | --- | --- |
| I | 170 ml | 0.249 g. |
| II | 191 | 0.0526 |
| III | 215 | 0.240 |
| IV | 160 | 0.409 |
| V | 240 | 0.428 |
| VI | 150 | 0.0784 |
| VII | 148 | 0.0411 |
| VIII | 165 | 0.0988 |

Bioassay, as above, showed most active fraction to be area VII (both vasodilator and Spasmogenic), and similar to fraction area IX from first column, above. Next most active was fraction area VI (vasodilator and smooth-muscle relaxing similar to fraction area VIII from above column.

Figure 4:
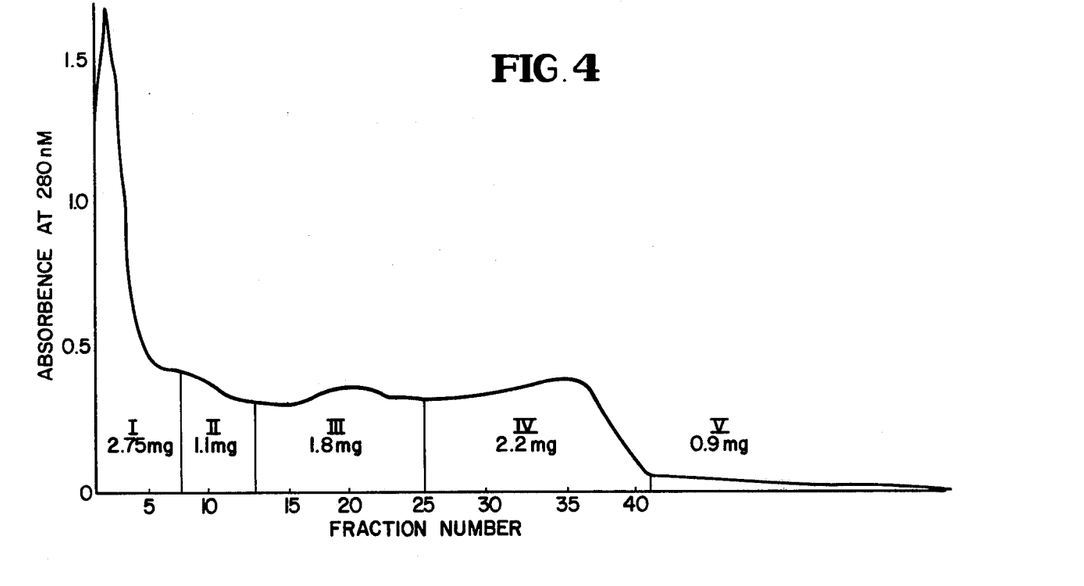
FIG. 4 represents a graph of the fractions obtained from a second CMC chromatography of the active fractions of area VII from FIG. 3.

G. Second Chromatography on CMC:

I. The fraction area IX from above described first CMC chromatography (I), performed on 2 separate occasions, were combined with the fraction area VII from the CMC chromatography (II), also described above, and these fractions were re-chromatographed on CMC, using the same buffer as before. Fractions were collected as shown in the attached FIG. 4. The most active fraction was that of area II, which elicited peripheral vasodilation in the dog, and contracted the following smooth muscle organs: rat stomach strip, rat colon, guinea pig ileum, guinea pig trachea, guinea pig gallbladder, guinea pig pulmonary artery, and guinea pig "lung".

Figure 5:
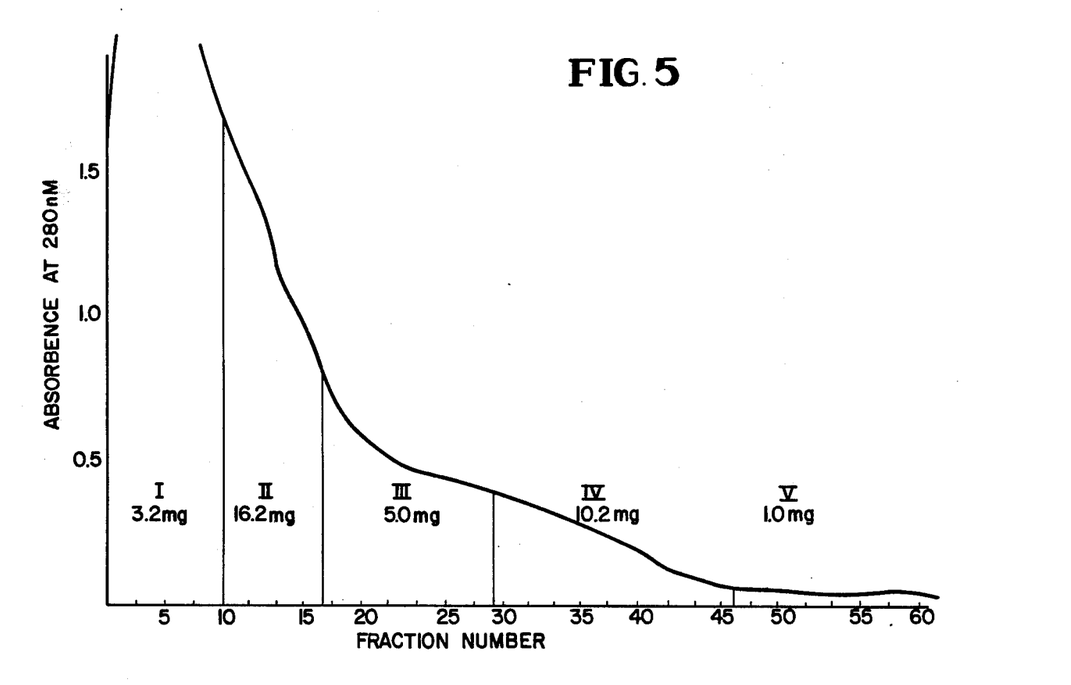
FIG. 5 represents a graph of the fractions obtained from a further CMC chromatography of the active fractions of areas VIII of FIG. 2 and area VI from FIG. 4.

II. The fraction area VIII from the first CMC chromatography (I), performed on 2 separate occasions, were combined with the fraction area VI from the CMC chromatography (II), also referred to above, and these fractions were rechromatographed on CMC, using the same buffer. Fractions were collected as shown in the attached FIG. 5. The most active fractions were those of area III and, somewhat weaker, those of area IV, which caused vasodilation in the dog, and relaxed the same tissues listed in the above paragraph (stomach, colon, ileum, trachea, gallbladder, pulmonary artery and "lung tissue").

These biological actions resemble those of porcine VIP and thus it is possible that this relaxant lung peptide may be closely related to VIP. Another property that strongly suggests this similarity is the strong cross-reaction between the relaxant lung peptide and VIP in a radioimmunoassay in which antibodies to porcine VIP are used (i.e., this lung peptide competes with VIP in binding to antibodies against the latter peptide).

The invention has been described herein by reference to certain preferred embodiments. However, as obvious variations thereon will become apparent to those skilled in the art, the invention is not to be considered as limited thereto.

What is claimed is:

1. The active polypeptide characterized as inducing peripheral vasodilation and systemic hypotension, and contracting non-vascular smooth muscle organs and being the fraction of hatched area B of FIG. 2, said polypeptide being a vasoactive material extracted and isolated from the lungs of animals, the process comprising the steps of collecting, boiling and mincing lung portions, extracting the resulting lung portions with acetic acid at a temperature of about 0°–5° C., filtering the resulting extract, and subjecting the extract to alginic acid absorption by the steps comprising lowering the pH with HCl acid and stirring with alginic acid, allowing the alginic acid mixture to settle and discarding supernatant liquid, recovering the resulting sediment, washing with dilute HCl and eluting from the alginic acid with HCl, adding sodium chloride to the eluate and collecting a salt precipitate, dissolving the salt precipitate in water, neutralizing the resulting solution to a pH of about 7, heating the solution with vigorous stirring and then extracting it with an alcohol, acidifying with mineral acid and collecting an alcoholic extract material, subjecting the alcoholic extract material to gel chromatography over a cross-linked dextran at least one time while dissolved in an organic acid, collecting fractions from the beginning of introduction of the extract into the chromatographic column, combining the recovered fractions, saturating with sodium chloride and salting out the product, collecting the fractions from the gel chromatography in two parts, testing for the most active fractions by tests of femoral blood flow on anesthetized dogs and on isolated smooth muscle organs, subjecting the active fractions to at least one ion-exchange chromatography over carboxymethyl cellulose while dissolved in a buffer solution at a pH of 6–7, centrifuging to eliminate insoluble materials, collecting separate fractions and treating with alginic acid for absorbtion of peptides and eluting with mineral acid, freeze drying and lyophilizing the resulting fractions, and identifying the separate active fractions by characterization on blood flow and smooth muscle organs.

* * * * *